United States Patent [19]
Gallistru et al.

[11] Patent Number: 5,107,019
[45] Date of Patent: Apr. 21, 1992

[54] PROCESS FOR PREPARING PARAFFIN-SULFONIC ACIDS

[75] Inventors: Onorio Gallistru, Monza; Artemio Gellera, Milan; Camilla Maraschin, Saronno; Cosimo Franco, San Donato Milanese; Giuseppe La Torre; Luciano Cavalli, both of Milan, all of Italy

[73] Assignee: Enichem Augusta S.p.A., Palermo, Italy

[21] Appl. No.: 534,769

[22] Filed: Jun. 7, 1990

[30] Foreign Application Priority Data

Jun. 15, 1989 [IT] Italy .................. 20878 A/89

[51] Int. Cl.$^5$ ............................................ C07C 303/00
[52] U.S. Cl. .................................... 562/124; 562/121
[58] Field of Search ................................ 562/121, 124

[56] References Cited

U.S. PATENT DOCUMENTS

| | | | |
|---|---|---|---|
| 4,310,473 | 1/1982 | Springmann | 562/124 |
| 4,557,873 | 12/1985 | Pistorius | 562/124 |
| 4,778,945 | 10/1988 | Faggian | 562/124 |
| 4,798,915 | 1/1989 | Faggian | 562/124 |
| 4,808,343 | 2/1989 | Pistorius | 562/124 |

FOREIGN PATENT DOCUMENTS

| | | | |
|---|---|---|---|
| 46-13374 | 4/1971 | Japan | 562/121 |
| 1194699 | 6/1970 | United Kingdom | 562/121 |

*Primary Examiner*—Alan Siegel
*Attorney, Agent, or Firm*—Hedman, Gibson & Costigan

[57] ABSTRACT

The invention is concerned with an improved process for preparing paraffin-sulfonic acids containing from 10 to 20 carbon atoms, as well as their salts. The process comprises the initial reaction of sulfo-oxidation of the concerned mixture of n-paraffins, the removal of unreacted n-paraffins from the reaction mixture, the removal of the excess of $SO_2$ from said mixture, and the removal from the reaction mixture of the therein formed sulfuric acid, with the simultaneous recovery of the end product.

After the removal of $SO_2$, to the reaction mixture hydrogen peroxide is added and the so obtained solution is submitted to one treatment selected from among the following treatments:
(a) addition of an alcohol with a number of carbon atoms comprised within the range of from 4 to 8;
(b) heating up to a temperature comprised within the range of from 50° to 150° C. and vacuum distillation under a residual pressure comprised within the range of from 5 to 500 mm$_{Hg}$ until at least 60% of contained water is distilled off;
(c) addition of an either aliphatic or cycloaliphatic paraffin with a number of carbon atoms comprised within the range of from 6 to 8 and distillation of the resulting azeotropic mixture at a temperature comprised within the range of from 20° to 120° C.

7 Claims, No Drawings

PROCESS FOR PREPARING PARAFFIN-SULFONIC ACIDS

The present invention is concerned with an improved process for preparing paraffin-sulfonic acids with a number of carbon atoms comprised within the range of from 10 to 20, as well as their salts. The process is based on the reaction of sulfo-oxidation of the concerned mixture of n-paraffins and on the removal from said reaction mixture of the therein formed sulfuric acid, which process is characterized by the addition of hydrogen peroxide to the reaction mixture before sulfuric acid is removed from it, and in that this removal of sulfuric acid is accomplished according to some particular treatments selected, alternatively to one another, from among such treatments as specified in the following.

From U.K. patent No. 1,194,699 to Hoechst it is known to prepare paraffin-sulfonic acids with a number of carbon atoms comprised within the range of from 10 to 20, by means of the sulfo-oxidation of n-paraffins with the same number of carbon atoms, with $SO_2$ and $O_2$ in the presence of water and using U.V. light in order to initiate said reaction.

The raw reaction product obtained from the sulfo-oxidation reactor is constituted by a mixture containing low percentages of paraffin-sulfonic acids, water, sulfuric acid, organic byproducts deriving from secondary reactions and, prevailingly, by unreacted n-paraffins.

After a preliminary separation of a portion of sulfuric acid by heating to about 100° C., the raw reaction product is distilled at temperatures comprised within the range of from 60° to 180° C., with two phases being formed. The bottom phase is aqueous sulfuric acid, which is removed, and the top phase contains the unreacted n-paraffins and paraffin-sulfonic acids deprived of sulfuric acid.

The process disclosed in above said patent must mandatorily be carried out continuously, if one wants to avoid the formation of a product with colour characteristics which would render it unsuitable for the following uses.

From U.S. Pat. No. 4,686,097, it is known as well that the removal of sulfuric acid from the reaction mixture constituted by alkane-sulfonic acid, unreacted n-paraffins, $SO_2$, $H_2O$ and $H_2SO_4$, can be improved by means of a process according to which $SO_2$ is initially vented and most $H_2SO_4$ is removed, according to as provided by U.K. patent No. 1,194,699, and to the so obtained concentrated mixture an alkali-metal compound (i.e., a salt, a peroxide or a hydroxide) is added: in that way, the residual sulfuric acid is transformed into bisulfate, which is removed.

However, the reported method, while is still affected by the drawback of a preliminary removal of most sulfuric acid, introduces an additional operating step with a solid body being formed, which could anyway cause problems, and, from the view point of the processes carried out batchwise, does not eliminate the drawback of the undesired formation of coloured useful product.

From Dutch patent application No. 6,812,646, it is known as well that light-coloured alkane-sulfonic acids, not containing sulfuric acid, can be prepared by means of a process according to which the reaction of sulfo-oxidation is carried first and the resulting solution is then heated at a temperature higher than 140° C., in the presence of $H_2O_2$ and under pressures higher than 4 atmospheres: this drastic treatment causes the nearly total dissociation of sulfuric acid and the formation of an aqueous solution composed by alkane-sulfonic acids, paraffinic hydrocarbons and a residual amount of sulfuric acid, which can be further removed by treatment under vacuum, at temperatures lower than 100° C.

The present Applicant has found now that paraffin-sulfonic acids with a number of carbon atoms comprised within the range of from 10 to 20, and their salts, free, or substantially free, from any residues of sulfuric acid, can be prepared without intermediate solid bodies being formed, and with no need of resorting to the use of drastic conditions of temperature and pressure: the product which is formed is endowed with all of the desired characteristics, in view of any possible successive applications.

In fact, the object of the instant invention is a process for preparing paraffin-sulfonic acids, and their salts, containing a number of carbon atoms comprised within the range of from 10 to 20, comprising the initial reaction of sulfo-oxidation of the concerned mixture of n-paraffins the removal of unreacted n-paraffins from the reaction mixture, the removal of the excess of $SO_2$ from said mixture, and the removal from said reaction mixture of the therein formed sulfuric acid, with the end product being simultaneously recovered, characterized in that, after the removal of $SO_2$, to the reaction mixture hydrogen peroxide is added and the so obtained solution is submitted to one treatment selected from among the following treatments:

(a) addition of an alcohol with a number of carbon atoms comprised within the range of from 4 to 8;

(b) heating up to a temperature comprised within the range of from 50° to 150° C. and vacuum distillation under a residual pressure comprised within the range of from 5 to 500 $mm_{Hg}$ until at least 60% of contained water is distilled off;

(c) addition of an either aliphatic or cycloaliphatic paraffin with a number of carbon atoms comprised within the range of from 6 to 8 and distillation of the resulting azeotropic mixture at a temperature comprised within the range of from 20° to 110° C.

Hydrogen peroxide is added to the reaction mixture at a concentration comprised within the range of from 40 to 120 volumes, in an amount comprised within the range of from 0.5 to 5% relatively to the above said mixture.

As said, the so obtained mixture can be submitted to a particular treatment in order to remove sulfuric acid formed in said reaction mixture, and recover the end product. As already seen, said treatment can be selected from among the following treatments:

(a) addition of an alcohol with a number of carbon atoms comprised within the range of from 4 to 8;

(b) heating up to a temperature comprised within the range of from 50° to 150° C. and vacuum distillation under a residual pressure comprised within the range of from 5 to 500 $mm_{Hg}$ until at least 60% of contained water is distilled off;

(c) addition of an either aliphatic or cycloaliphatic paraffin with a number of carbon atoms comprised within the range of from 6 to 8 and distillation of the resulting azeotropic mixture at a temperature comprised within the range of from 20° to 110° C.

In the first case, to the mixture an alcohol with a number of carbon atoms comprised within the range of from 4 to 8, preferably hexanol, is added, which causes the separation to take place of a heavy phase containing nearly all of $H_2SO_4$, which is thus removed, whilst the light phase is neutralized with alkali-metal hydroxides, with the salts of the paraffin-sulfonic acids being hence obtained after the removal of the n-paraffins still contained in the reaction mixture.

In the second case, after the addition of $H_2O_2$, the mixture is heated under vacuum to the temperature of 50°–150° C., and is simultaneously submitted to a distillation under a residual pressure comprised within the range of from 5 to 500 mm$_{Hg}$, so as to remove not less than 60% of the water contained in the system.

After such a treatment, two phases are obtained, which are constituted as follows:

Light Phase: containing the paraffin-sulfonic acids, n-paraffins, water and residual sulfuric acid;

heavy phase: constituted by a mixture of water and sulfuric acid, in which sulfuric acid has a concentration comprised within the range of from 25 to 70% as a function of the preceding distillation treatment.

The light phase of the above described double-phase system has a composition comprised within the following range:

| paraffin-sulfonic acids | 35–41% by weight |
| n-paraffins ($C_{10}$–$C_{20}$) | 50–55% by weight |
| sulfuric acid | 2–7% by weight |
| water | 2–8% by weight |

Such a phase is submitted to an extraction with supercritic $CO_2$, according to as disclosed in U.S. Pat. No. 4,843,184 to the same Applicant's name, whose text is herein incorporated by reference in its entirety.

In particular, still with reference to the above cited U.S. Pat. No. the conditions of extraction of the above said phase with supercritic $CO_2$, result to be the following:

extraction temperatures comprised within the range of from 32° to 80° C.;

extraction pressure comprised within the range of from 75 to 350 bar;

weight ratio of supercritic $CO_2$, used for the extraction of the residual solution, to the paraffinsulfonic acids contained in the reaction mixture, comprised within the range of from 1:1 to 50:1.

The mixture of paraffin-sulfonic acids resulting from this latter process can be generally neutralized in a way known from the prior art with any desired bases, with paraffin-sulfonates of any desired types being hence obtained.

In the (c) case, the solution obtained after the addition of $H_2O_2$ is submitted to a continuous treatment in order to remove water and sulfuric acid, according to which treatment an aliphatic paraffin, with a number of carbon atoms comprised within the range of from 6 to 8, or a cycloaliphatic paraffin, is added, which forms an azeotropic mixture with the water contained in the above said mixture, said azeotropic mixture is heated up to a temperature comprised within the range of from 20° to 110° C., and is simultaneously submitted to an azeotropic distillation under a residual pressure comprised within the range of from 5 to 760 mm$_{Hg}$.

After such a treatment, two phases are obtained, which are constituted as follows:

Light phase: containing the paraffin-sulfonic acids, n-paraffins, residual water, residual sulfuric acid and the azeotropic mixture forming agent;

heavy phase: constituted by a mixture of water and sulfuric acid, in which sulfuric acid has a concentration comprised within the range of from 25 to 70% as a function of the preceding azeotropic distillation treatment.

The light phase of the above described double-phase system, after the removal of the azeotropic mixture forming agent by distillation under vacuum, has a composition comprised within the following range:

| paraffin-sulfonic acids | 40–55% by weight |
| n-paraffins ($C_{10}$–$C_{20}$) | 45–60% by weight |
| sulfuric acid | 0.5–4% by weight |
| water | 0.1–2% by weight |

Such as phase is submitted to an extraction with supercritic, $CO_2$, according to as disclosed in already cited U.S. Pat. No. 4,843,184 to the same Applicant's name.

In particular, still with reference to the above cited U.S. Pat. No., the conditions of extractions of the above said phase with supercritic $CO_2$/ result to be the following:

extraction temperatures comprised within the range of from 32° to 80° C.;

extraction pressure comprised within the range of from 75 to 350 bar;

weight ratio of supercritic $CO_2$, used for the extraction of the residual solution, to the paraffin-sulfonic acids contained in the reaction mixture, comprised within the range of from 1:1 to 50:1.

The mixture of paraffin-sulfonic acids resulting from this latter process can be generally neutralized in a way known from the prior art, with any desired bases, with paraffin-sulfonates of any desired types being hence obtained.

In the following some examples are reported with the purpose of illustrating the same invention without limiting it.

EXAMPLE NO. 1

222.5 g of a raw reaction mixture of paraffin-sulfonic acids (from which decantable n-paraffins and $SO_2$ have been removed), obtained by means of the sulfo-oxidation of ($C_{10}$–$C_{20}$)-n-paraffins, is treated in a flask of 500 ml of capacity with 2.3 g of $H_2O_2$ (80 volumes). The solution is heated to the temperature of 60°–70° C., then 55.6 g of n-hexyl alcohol is added.

After phase decantation, 80.7 g of heavy phase and 192.2 g of light phase, containing the paraffin-sulfonic acids, n-hexyl alcohol and traces of $H_2O$ and $H_2SO_4$ are separated.

EXAMPLE NO. 2

To 160 g of a raw reaction mixture of paraffin-sulfonic sulfonic acids (from which decantable n-paraffins and $SO_2$ have been removed), obtained by means of the sulfooxidation of ($C_{10}$–$C_{20}$)-n-paraffins, 1.9 g of $H_2O_2$ (60 volumes) is added. The solution is heated to the temperature of 60°–70° C., then 40 g of n-hexyl alcohol is added.

The two phases are separated by centrifugation. The light phase, of 144.7 g, contains all of the paraffin-sulfonic acids, n-hexyl alcohol and traces of $H_2O$ and $H_2SO_4$.

EXAMPLE 3

A distillation equipment was used, which essentially consisted of a flask to which the mixture was charged, a condenser in order to cool the vapours, a content collecting vessel and a vacuum pump.

200 g of a raw reaction mixture having the following compositions:

| | |
|---|---|
| paraffin-sulfonic acids | 22.4% |
| n-paraffins | 31.3% |
| sulfuric acid | 8.4% |
| water | 38% | was charged to a flask, to it 1 g of $H_2O_2$ (80 volumes) was added and the resulting mixture was stirred. Vacuum was applied to the flask, with a residual pressure of 30 $mm_{Hg}$ being obtained, and then the flask was heated, such as to cause 69.7 g of $H_2O$ to distill off.

The pressure inside the flask was increased back up to atmospheric pressure, and 18.15 g of a heavy phase containing 67.45% of $H_2SO_4$ and 107 g of light phase were discharged. Said light phase had the following composition:

| | |
|---|---|
| paraffin-sulfonic acid | 41% by weight |
| n-paraffins | 54% by weight |
| sulfuric acid | 2.3% by weight |
| water | 2.6% by weight |

102.3 g of such a light phase was submitted to an extraction with supercritical $CO_2$.

The extraction was carried out at 45° C. and 150 bar; the flow rate of $CO_2$ was kept constant; one hour later, the feed of $CO_2$ was discontinued and the refined product contained inside the extractor was discharged.

The analysis of such a product gave the following results:

| | |
|---|---|
| paraffin-sulfonic acid | 88.85% by weight |
| n-paraffins | 0.55% by weight |
| sulfuric acid | 4.95% by weight |
| water | 5.60% by weight |

Extracted n-paraffins are pure and can be recycled to the sulfo-oxidation reactor.

EXAMPLE NO. 4

1,000 g of raw reaction mixture (having the same composition as of the raw reaction mixture of Example No. 3) was charged to a flask and to it 9.5 g of $H_2O_2$ (80 volumes) was added.

The solution was heated up to its boiling point, was allowed to reflux for about 5 minutes and then was cooled down to 90° C.

Under these conditions, the solution separated into two phases: the heavy phase, of 153.4 g, was constituted by water and sulfuric acid at 25% by weight, and the light phase, of 854.6 g, had the following composition:

| | |
|---|---|
| paraffin-sulfonic acid | 28.4% by weight |
| n-paraffins | 39.1% by weight |
| sulfuric acid | 5.5% by weight |
| water | 27.7% by weight |

After phase separation, 497.7 g of the light phase was submitted to vacuum distillation in the same equipment as of Example No. 3.

Under a residual pressure of 20 $mm_{Hg}$ and at the temperature of 80° C., 116.3 of water, equivalent to 84.36% of initially contained water, was distilled.

After distillation, the residual mixture separated into two phases: the heavy phase, of 33.9 g, contained 55.7% of sulfuric acid, and the light phase, of 349.3 g, had the following composition:

| | |
|---|---|
| paraffin-sulfonic acid | 40.2% by weight |
| n-paraffins | 55.35% by weight |
| sulfuric acid | 2.2% by weight |
| water | 2.9% by weight |

114.9 g of such a mixture was submitted to an extraction with supercritical $CO_2$.

The extraction was carried out at 45° C. and 150 bar.

The end refined reaction product has the following composition:

| | |
|---|---|
| paraffin-sulfonic acid | 88.05% by weight |
| n-paraffins | 0.25% by weight |
| sulfuric acid | 4.85% by weight |
| water | 6.30% by weight |

EXAMPLE NO. 5

49.7 g of a raw solution of paraffin-sulfonic acids, obtained by means of the sulfo-oxidation of $(C_{10}-C_{20})$-n-paraffins, deprived of decantable n-paraffins and of $SO_2$, and having the following composition:

| | |
|---|---|
| paraffin-sulfonic acids | 28.1% by weight |
| sulfuric acid | 5.5% by weight |
| water | 26.6% by weight |
| n-paraffins | 39.8% by weight | and to which 0.5 g of $H_2O_2$ at 80 volumes were added, was charged to a flask of 0.5 litre of capacity and was treated with 251.7 g of n-heptane.

The solution was submitted to a distillation at a temperature comprised within the range of from 20° to 40° C. and under a pressure comprised within the range of from 30 to 40 $mm_{Hg}$.

In that way, 10.12 g of water was distilled off, whilst n-heptane was recycled to the distillation flask. Inside the flask the solution separated into two phases: the heavy phase, of 3.9 g, was constituted by $H_2SO_4$ at 55.8%, and the light phase, of 271 g, had the following composition:

| | |
|---|---|
| paraffin-sulfonic acids | 5.30% by weight |
| $H_2SO_4$ | 0.18% by weight |
| $H_2O$ | 0.70% by weight |
| $(C_{10}-C_{20})$-n-paraffins | 7.15% by weight |
| n-heptane | 86.50% by weight |

After distilling off all of n-heptane, said light phase was submitted to an extraction with supercritical $CO_2$.

The extraction was carried out at 45° C. and 150 bar; the flow rate of $CO_2$ was kept at a constant value.

One hour later, the feed of $CO_2$ was discontinued and the refined product contained inside the extractor was discharged.

The analysis of such a product gave the following results:

| | |
|---|---|
| paraffin-sulfonic acids | 85.30% by weight |
| $H_2SO_4$ | 2.90% by weight |
| $H_2O$ | 11.20% by weight |
| n-paraffins | 0.50% by weight |

Extracted n-paraffins were pure and could be recycled to the sulfo-oxidation reactor.

EXAMPLE NO. 6

78.21 g of raw reaction mixture (deprived of decantable n-paraffins and of the excess of $SO_2$), containing the paraffin-sulfonic acids obtained by means of the sulfo-oxidation of ($C_{10}$–$C_{20}$)-n-paraffins and having the same composition as of Example No. 5, was charged to a flask of 1 litre of capacity, and to it 0.89 g of $H_2O_2$ (80 volumes) and 394.59 g of n-heptane were added.

The solution was submitted to a distillation at a temperature comprised within the range of from 85 to 104° C and under the atmospheric pressure.

16.4 g of water was distilled off, whilst n-heptane was recycled to the distillation flask.

Inside the flask two phases separated, in which the heavy phase, of 8.45 g, was constituted by an aqueous solution of sulfuric acid at 42.4%, and the light phase, of 447.8 g, had the following composition:

| | |
|---|---|
| paraffin-sulfonic acids | 4.90% by weight |
| $H_2O$ | 0.02% by weight |
| $H_2SO_4$ | 0.08% by weight |
| ($C_{10}$–$C_{20}$)-n-paraffins | 7.49% by weight |
| n-heptane | 87.50% by weight |

After distilling off all of n-heptane under vacuum, said light phase was submitted to an extraction with supercritical $CO_2$.

The extraction was carried out at 45° C. and 150 bar; the flow rate of $CO_2$ was kept constant.

After one hour, the feed of $CO_2$ was discontinued and the refined product contained inside the extractor was discharged.

The analysis of the obtained product gave the following results:

| | |
|---|---|
| paraffin-sulfonic acids | 97.20% by weight |
| $H_2SO_4$ | 1.60% by weight |
| $H_2O$ | 0.50% by weight |
| n-paraffins | 0.60% by weight |

Extracted n-paraffins were pure and could be recycled to the sulfo-oxidation reactor.

We claim:

1. A process for preparing paraffin sulfonic acids containing from 10 to 20 carbon atoms, as well as their salts, said process comprising the following steps in succession:
    (a) sulfo-oxidating a mixture of n-paraffins to form a reaction mixture comprising paraffin-sulfonic acids, unreacted n-paraffins, $SO_2$, sulfuric acid and water;
    (b) removing unreacted n-paraffins from the reaction mixture;
    (c) removing excess $SO_2$ from the mixture obtained in step (b);
    (d) adding hydrogen peroxide to the reaction mixture obtained in step (c);
    (e) removing sulfuric acid and simultaneously recovering paraffin-sulfonic acids from the reaction mixture obtained in step (d) by:
        (i) adding an alcohol having from 4 to 8 carbon atoms to the mixture obtained in step (d); or
        (ii) heating the mixture obtained in step (d) to a temperature of from 50° C. to 150° C. and vacuum distilling at a residual pressure of from 5 to 500 $mm_{Hg}$ to distill off at least 60 percent of the water present in the mixture; or
        (iii) adding either an aliphatic or cycloaliphatic paraffin having from 6 to 8 carbon atoms to form an azeotropic mixture and distilling said azeotropic mixture at a temperature of from 20° to 100° C.

2. A process as defined in claim 1 wherein said alcohol of step (e)(i) comprises hexanol.

3. A process as defined in claim 1 wherein step (e)(ii) further comprises extracting the resulting solution with supercritical $CO_2$.

4. A process as defined in claim 1 wherein said aliphatic paraffin of step (e)(ii) comprises n-heptane.

5. A process as defined in claim 1 wherein said cycloaliphatic paraffin of step (e)(ii) comprises cyclohexane.

6. A process as defined in claim 1 wherein said step (e)(iii) further comprises extracting the resulting solution with supercritical $CO_2$.

7. A process as defined in claim 1 wherein in step (d) hydrogen peroxide is added at a temperature of from 40 to 120 volumes in an amount of from 0.5 to 5 weight percent based on the weight of the mixture.

* * * * *